United States Patent [19]

Schmidt-Gollwitzer et al.

[11] Patent Number: 6,027,749

[45] Date of Patent: Feb. 22, 2000

[54] PHARMACEUTICAL COMBINED PREPARATION, KIT AND METHOD FOR HORMONAL CONTRACEPTION

[75] Inventors: Karin Schmidt-Gollwitzer; Walter Klemann, both of Berlin, Germany

[73] Assignee: Schering AG, Germany

[21] Appl. No.: 08/981,488

[22] PCT Filed: Jun. 27, 1996

[86] PCT No.: PCT/DE96/01192

§ 371 Date: Jun. 3, 1998

§ 102(e) Date: Jun. 3, 1998

[87] PCT Pub. No.: WO97/01342

PCT Pub. Date: Jan. 16, 1997

[30] Foreign Application Priority Data

Jun. 28, 1995 [DE] Germany .......................... 195 25 017

[51] Int. Cl.[7] .............................. A61K 9/20; A61K 31/56
[52] U.S. Cl. .......................... 424/464; 514/170; 514/843
[58] Field of Search ............................ 424/464; 514/170, 514/843

[56] References Cited

U.S. PATENT DOCUMENTS 5,756,490  5/1998  Lachnit et al. .......................... 517/170

*Primary Examiner*—James M. Spear
*Attorney, Agent, or Firm*—Millen, White, Zelano & Branigan, P.C.

[57] ABSTRACT

The present invention describes a two-stage pharmaceutical combined preparation for hormonal contraception containing at least 30 daily unit doses, which preparation, in its first stage, comprises as hormonal active ingredient a combination of an oestrogen preparation and, in a dose that is at least sufficient to inhibit ovulation, a gestagen preparation, in single stage form and, in the second stage comprises as hormonal active ingredient an oestrogen preparation only, wherein the first stage comprises a minimum of 25 and a maximum of 77 daily discrete or continuous unit doses and the second stage comprises 5, 6 or 7 daily discrete or continuous unit doses, and wherein the total number of daily units is equal to the total number of days of the desired cycle of a minimum of 30 and a maximum of 84 days. This combined preparation, in the form of a monthly pack, which is used for female fertility control, permits as low as possible an oestrogen content in each individual unit dose and also has a low total hormone content per cycle of administration, with high contraceptive reliability, low incidence of follicle development, and satisfactory cycle control with reliable avoidance of intermediate bleeding as well as undesired side effects.

40 Claims, No Drawings

PHARMACEUTICAL COMBINED PREPARATION, KIT AND METHOD FOR HORMONAL CONTRACEPTION

This application is a 371 of PCT/DE96/01192 filed Jun. 27, 1996.

DESCRIPTION

The present invention relates to a two-stage pharmaceutical combined preparation for hormonal contraception containing at least 30 daily unit doses, which preparation, in its first stage, comprises as hormonal active ingredient a combination of an oestrogen preparation and, in a dose that is at least sufficient to inhibit ovulation, a gestagen preparation, in single stage form and, in the second stage comprises as hormonal active ingredient an oestrogen preparation only, wherein the first stage comprises a minimum of 25 and a maximum of 77 daily discrete or continuous unit doses and the second stage comprises 5, 6 or 7 daily discrete or continuous unit doses, and wherein the total number of daily units is equal to the total number of days of the desired cycle of a minimum of 30 and a maximum of 84 days, and relates also to a corresponding pack (contraceptive kit) containing that combined preparation, and to a contraceptive method that uses the above contraceptive preparation.

Oral contraceptives in the form of combined preparations have been known since 1960 as so-called monophase preparations. Those preparations consist of 21 unit doses that comprise active ingredient and 7 tablets or dragées that are active ingredient-free. The daily unit dose is composed of an oestrogen and gestagen. In monophase preparations the dose of active ingredient to be administered daily is the same in each unit dose. If the dose that is to be administered daily of the active components in the individual unit doses is different in individual sections over the administration cycle, then the preparation is referred to as a so-called multi-phase preparation. Triquilar® may be mentioned as an especially well-known example (DE-AS 23 65 103).

As a result of the development of new, more active gestagens than those contained in the first oral contraceptives, a continuous reduction of the daily dose of gestagen has been possible. It has also been possible for the daily dose of oestrogen to be reduced although, as before, the oestrogen contained in hormonal contraceptives is usually ethynyloestradiol. In the development of new, improved oral contraceptives, the following three factors have been (and are) dominant:
(1) contraceptive reliability
(2) good cycle control, that is to say a low incidence of intermediate bleeding and
(3) a minimum of undesired side effects should be ensured.

The contraceptive reliability is effected in particular by the gestagenic component. The daily dosage amount of that component corresponds at least to the threshold dose considered necessary for the gestagen in question to inhibit ovulation. The ethynyloestradiol usually used as the oestrogen in combined preparations should increase the ovulation-inhibiting effect of the gestagen and in particular ensure stability of the cycle. In the case of administration of ethynyloestradiol alone, the daily dose that has to be used in order to inhibit ovulation is 100 $\mu$g.

Combined preparations with the most recent generation of gestagens are, for example, the monophase preparations Femovan (DE-PS 2 546 062) and Marvelon (DE-OS 2 361 120). Milvane® may be mentioned as an example of a multi-phase preparation in which the unit doses contain a gestagen of the most recent generation, namely gestodene (EP-0 148 724). In those three-phase preparations, usually 4–6 dragées are administered in the first phase, each dragée comprising a low dose of oestrogen and a low dose of gestagen. In the second phase of 4–6 dragées, each unit dose comprises an oestrogen in the same dose or a dose that is slightly increased (up to a maximum of twice) and a gestagen in the same dose or a in a dose that is slightly increased (up to a maximum of 1.5 times). In a third phase of 9–11 units, each dragée comprises an oestrogen in the same dose or a dose that is slightly reduced, at most reduced to the initial amount, and a gestagen in a dose that is further increased, to a maximum of 3 times the initial amount. 7 pill-free days then follow.

Recently, multi-phase combined preparations have been proposed that may provide an extended administration of active ingredient-containing unit doses, that is to say of up to 24 days in the 28-day cycle. In those preparations the daily dose of gestagen either increases from the first, over the second, up to the third phase (EP-A 0 491 415) or decreases (EP-A 0 491 438). In order to complete the 28-day cycle, in the first case there follow 4 blind pill days, 4 placebos or 4 unit doses that contain gestagen only, and in the second case from 4 to 7 blind pill days or from 4 to 7 placebos.

The aim of the development of new oral contraceptives having a reduced daily hormone dose is to minimize the side effects described in epidemiological studies. More recent epidemiological data point towards a trend for the improved tolerability of low-dose preparations in respect of cardiovascular side effects [Thorogood M, Oral Contraceptives and Cardiovascular Disease: an Epidemiologic Overview; Pharmacoepidemiology and Drug Safety, Vol. 2: 3–16 (1993); Gerstman B. B., Piper J. M., Tomita D. K., Ferguson W. J., Stadel B. V., Lundin F. E.; Oral Contraceptive Estrogen Dose and the Risk of Deep Venous Thromboembolic Disease, Am. J. E., Vol.133, No. 1, 32–36 (1991); Lidegaard O., Oral contraception and the risk of a cerebral thromboembolic attack: results of a case-control study; BMJ Vol. 306, 956–63 (1993); Vessey M., Mant D., Smith A., Yeates D., Oral contraceptives and venous thromboembolism: findings in a large prospective study; BMJ, Vol. 292 (1986); Mishell D. R., Oral Contraception: Past, Present and Future Perspectives; Int. J. Fertil., 36 Suppl., 7–18 (1991)].

A connection between the level of the daily oestrogen dose and the frequency of cardiovascular complications is accepted.

The preparation currently having the lowest dose of oestrogen is marketed as Mercilon® and contains 20 $\mu$g of ethynyloestradiol in combination with 150 $\mu$g of desogestrel in each daily unit dose over a period of 21 days with a following pill-free period of 7 days. As is to be expected, the cycle control of that preparation by comparison with preparations having a higher dose of oestrogen is somewhat poorer. A further clinically significant problem is the observation, which has been made in several studies, of a lower ovarian suppression of the preparation containing 20 $\mu$g of ethynyloestradiol. Clearly, below that very low dose of oestrogen, ripening of follicles occurs in many women, which could be detected by ultrasound examinations and hormone tests [Lunell N. O., Carlstrom K., Zador G., Ovulation inhibition with a combined oral contraceptive containing 20 $\mu$g ethynyloestradiol and 250 $\mu$g levonorgestrel; Acta Obstet. Gynecol. Scand. Suppl. 88: 17–21 (1979); Mall-Haefeli M., Werner-Zodrow I., Huber P. R., Klinische Erfahrungen mit Mercilon und Marvelon unter besonderer Berücksichtigung der Ovar-Funktion (Clinical experiences with Mercilon and Marvelon with special consideration given to ovary function); Geburtsh. and Frauenheilk. 51, 35–38, Georg Thieme Verlag, Stuttgart-New York (1991); Strobel E., Behandlung mit oralen Kontrazeptiva (Treatment with oral contraceptives); Fortschr. Med. 110 Jg. No. 20 (1992); Letter to Editor, Contraception 45: 519–521 (1992); Teichmann A. T., Brill K., Can Dose Reduction of Ethynylestradiol in OCs Jeopardize Ovarian Suppression and Cycle Control? Abstract Book, VIIIth World Congress on Human Reproduction, Bali, Indonesia (1993)].

Until recently, several days, interruption of the administration of dragées containing active ingredient was considered necessary in order to trigger withdrawal bleeding and ensure adequate cycle control.

Other preparations have been described that contain an oestrogenic and gestagenic active ingredient and that are generally administered in constant amounts in each individual unit dose over a period of 21 days, the administration of those unit doses containing an oestrogenic and gestagenic active ingredient preceding the administration of unit doses containing oestrogen only (Ijzerman, U.S. Pat. No. 3,502, 772; Pasquale, U.S. Pat. No. 4,921,843; Kuhl et al., EP-A 0 499 348). With those preparations, at the beginning of administration, either already on the first day of the cycle (Kuhl) or at the earliest on the second day of the cycle (Pasquale), the administration is begun of unit doses that contain an oestrogenic active ingredient only, at a dose that is below the ovulation-inhibiting dose of the oestrogenic component so that, especially in the first cycle of administration, follicle development may occur. Follicle development is considered responsible for breakthrough ovulation (Chowdry et al., "Escape" ovulation in women due to the missing of low dose combination oral contraceptive pills, Contraception, 22: 241–247, 1980; Molloy B. G. et al., "Missed pill" conception: fact or fiction? Brit. Med. J. 290, 1474–1475, 1985). The contraceptive protection is consequently placed in question. The risk of a pregnancy is therefore high especially in the case of mistakes in administration among the 20 µg ethynyloestradiol preparations.

DE-OS 43 13 926 describes a pharmaceutical preparation for contraception having a minimum of four phases, which preparation consists of a fixed or sequential combination, consisting of a minimum of three phases, of ethynyloestradiol or mestranol or another synthetic oestrogen, and also a gestagen, and an oestrogen preparation that is to be administered at least in the fourth phase of the cycle and that contains ethynyloestradiol or mestranol and/or another synthetic and/or endogenous oestrogen. That preparation is to be administered over the entire cycle of the woman and is limited to a 28-day administration.

Common to all preparations for hormonal contraception on the market so far is that the pack unit is set to a 28-day cycle of administration (4-week rhythm). For a prevention period of one year, that is to say 12 months, administration of the contents of 13 pack units is therefore necessary.

It has, of course, already been known for a long time that the onset of menstruation, when taking an oral contraceptive where there is a continuous daily administration of both oestrogen-containing and especially gestagen-containing unit doses, can be deferred until completion of the administration of the gestagen-containing unit doses [Hamerlynck J. V. Th. H. et al., Contraception 35,3: 199–205 (1987); Luodon N. B., IPPF Med. Bull. 13,1: 2–3 (1979); Luodon N. B. et al., Brit. Med. J. 60085: 487–490 (1977/2)]. After stopping the gestagen-containing unit doses withdrawal bleeding commences. Although the ovulation-inhibiting agent according to EP-A 0 499 348 is not limited to a desired administration cycle of 28 days, the number of hormone day units containing both oestrogen and gestagen is restricted to an upper limit of 23 day units.

The aim of the present invention is to provide a combined preparation having as low as possible an oestrogen content in each individual unit dose but at the same time also a low total hormone content per cycle of administration, with which, with a high degree of contraceptive reliability, as low as possible an incidence of follicle development even in the first cycle of administration, and satisfactory cycle control with reliable prevention of intermediate bleeding, such as breakthrough bleeding and spotting, are achieved and with which undesired side effects are avoided.

This aim is achieved by the provision of the two-stage combined preparation described at the outset and also a corresponding pack containing that combined preparation (contraceptive kit) and a contraceptive method that uses the described contraceptive preparation.

Preferred arrangements of the present invention concern a pharmaceutical combined preparation of the type mentioned at the outset in which the first stage comprises 25 or 26 daily unit doses, the first stage comprises a minimum of 28 and a maximum of 84 daily unit doses, the first stage comprises 28 daily unit doses, the first stage comprises 28 plus 7, or 28 plus a multiple of 7, daily unit doses, the second stage comprises 7 daily unit doses, the first stage comprises 25 or 26 daily unit doses and the second stage comprises 5 or 6 daily unit doses, so that the combined preparation has a total of 30 or 31 daily unit doses.

The present invention relates furthermore to a contraceptive kit containing a minimum of 30 and a maximum of 84 daily unit doses each comprising at least one hormonal active ingredient, which kit has a first and a second stage, wherein, in its first stage, the kit comprises as hormonal active ingredient a combination of an oestrogen preparation and, in a dose at least sufficient to inhibit ovulation, a gestagen preparation, in a single stage form, and, in the second stage, comprises as hormonal active ingredient an oestrogen preparation only, the first stage comprising a minimum of 25 and a maximum of 77 daily discrete or continuous unit doses and the second stage comprising 5, 6 or 7 daily discrete or continuous unit doses, and the total number of daily units being equal to the total number of days of the desired cycle of a minimum of 30 and a maximum of 84 days.

Preferred contraceptive kits according to the present invention are characterised as follows:

the first stage comprises 25 or 26 daily unit doses, the first stage comprises a minimum of 28 and a maximum of 84 daily unit doses, the first stage comprises 28 daily unit doses, the first stage comprises 28 plus 7, or 28 plus a multiple of 7, daily unit doses, the second stage comprises 7 daily unit doses, the first stage comprises 25 or 26 daily unit doses and the second stage comprises 5 or 6 daily unit doses, so that the kit has a total of 30 or 31 daily unit doses.

In a further embodiment of the contraceptive kit according to the invention, some of the unit doses of the first stage are arranged in periodically repeating sub-units that are separated from one another spatially and/or by other markings.

Preferably, the unit doses are arranged in sub-units at the earliest from the 26th daily unit dose, the individual sub-units can be separated from one another by perforations or other means suitable for separation, 7 unit doses are contained in each of the separate sub-units, the first stage comprises 28 plus 7, or 28 plus a multiple of 7, daily unit doses, and/or the second stage comprises 7 daily unit doses.

In the case of the contraceptive method according to the invention, which employs the described combined preparation, in the first stage, commencing with the first day of the cycle, a unit dose comprising an oestrogen in combination with a gestagenic component is administered daily over a minimum period of 25 and a maximum period of 77 days. There then follows the second stage in which over the remaining period of the cycle, which cycle comprises a minimum of 30 and a maximum of 84 days, an oestrogen is administered over 5, 6 or 7 days. Thus a unit dose comprising a hormonal active ingredient is administered on every day of the cycle.

With administration of the combined preparation according to the invention, recruitment of the dominant follicle, which in the spontaneous cycle occurs during the first 6 days of the menstrual cycle, is efficiently suppressed. Thus, with the combined preparation of the present invention follicle development can be suppressed and consequently breakthrough ovulations avoided, thereby increasing contraceptive reliability. This is of great importance especially where mistakes are made in administration, particularly in the case of hormonal contraceptives having a low daily dose of ethynyloestradiol. Since 25% of women who take the pill are known to make mistakes (omitting unit doses or extending the interval between the daily administration of two unit doses to more than 24 hours) (Finlay I. G., Scott M. B. G.: Patterns of contraceptive pill-taking in an inner city practice. Br. Med. J. 1986, 293: 601–602), the combined preparation according to the invention, when used as an ovulation-inhibiting agent, increases contraceptive reliability. This is true in particular in the case of the lowest-dose preparations.

In particular, however, this higher number of daily unit doses comprising both oestrogen and gestagen results in an extension of the cycle and a reduced frequency of withdrawal bleeding. The subsequent stage, in which unit doses that comprise as hormonal active ingredient an oestrogenic component only are administered daily over 5, 6 or 7 days, ensures a withdrawal bleeding and causes a stimulation of progesterone receptors in the endometrium, as a result of which a reduced rate of intermediate bleeding compared with conventional low-dose preparations is achieved in the subsequent administration cycle.

In conjunction with the extended phase of administration of oestrogen- and gestagen-containing unit doses, for example an extension of the menstrual cycles to 30 or 31 days (monthly pack) is thus possible.

According to the preferred variants an optional postponement of the withdrawal bleeding up to day 77 is possible, the bleeding commencing after the unit doses comprising oestrogen and gestagen have been stopped.

A variable manipulation of the initiation of the withdrawal bleeding is possible with the contraceptive kit according to the present invention, in which the unit doses of the first stage, at the earliest from the 26th daily unit dose, are arranged in sub-units that can be separated from one another by perforations or some other suitable means of separation.

The contraceptive kit according to the invention is constructed, for example, in the form of a blister in which each individual segment, each of which preferably contains 7 unit doses of the first stage, can conveniently and easily be separated by means of perforations made in the base plate of the blister. It is, however, also possible for the sub-units each to be in the form of individual separate blisters or for the, for example, 28 unit doses of the first stage to be in a first blister and for the following unit doses of the first stage to be in a second blister in which sub-units can be separated from one another by perforations in the described manner.

Preferably, in all embodiments of the invention the oestrogen of the first hormone component is selected from the group of compounds 17β-oestradiol, ethynyloestradiol and 17β-oestradiol valerate and the gestagen is selected from the group of compounds dienogest gestodene, levonorgestrel, desogestrel, 3-ketodesogestrel, drospironenone, cyproterone acetate, norgestimate and norethisterone and also the oestrogen of the second hormone component is selected from the group of compounds 17β-oestradiol, ethynyloestradiol and 17β-oestradiol valerate.

Preferably, in the present invention the oestrogen of the first hormone component is contained in each daily unit dose in a dose of from 1.0 to 6.0 mg of 17β-oestradiol, from 0.015 to 0.025 mg of ethynyloestradiol, from 1.0 to 4.0 mg of 17β-oestradiol valerate and the gestagen is contained in each daily unit dose in a dose of from 1.0 to 3.0 mg of dienogest from 0.05 to 0.075 mg of gestodene, from 0.05 to 0.125 mg of levonorgestrel, from 0.06 to 0.15 mg of desogestrel, from 0.06 to 0.15 mg of 3-ketodesogestrel, from 1.0 to 3.0 mg of drospironenone, from 1.0 to 2.0 mg of cyproterone acetate, from 0.2 mg to 0.3 mg of norgestimate from 0.35 to 0.75 mg of norethisterone.

The second hormone component comprises the oestrogen in each daily unit dose preferably in an amount of from 1.0 to 6.0 mg of 17β-oestradiol, from 0.002 to 0.04 mg of ethynyloestradiol, from 1.0 to 4.0 mg of 17β-oestradiol valerate.

According to an especially preferred embodiment the second hormone component contains as oestrogen ethynyloestradiol in an amount of from 0.01 to 0.015 mg in each daily unit dose.

There come into consideration as oestrogen for the first and for the second hormone component especially ethynyloestradiol or the natural oestradiol.

Of the gestagens mentioned for the second hormone component attention is drawn to gestodene; levonorgestrel is also preferred.

17β-oestradiol valerate, which may be contained as the oestrogen both in the first and in the second hormone component, is mentioned only as a possible representative of those 17β-oestradiol esters; other homologous esters of that kind may also be used as the oestrogen component within the scope of the present invention.

The following Examples serve to illustrate the present invention in more detail:

EXAMPLE 1:

| Day | 1 | 2 | 3 | 4 | 5 | 6 | 7 |
|---|---|---|---|---|---|---|---|
| Composition | C | C | C | C | C | C | C |
| Day | 8 | 9 | 10 | 11 | 12 | 13 | 14 |
| Composition | C | C | C | C | C | C | C |
| Day | 15 | 16 | 17 | 18 | 19 | 20 | 21 |
| Composition | C | C | C | C | C | C | C |
| Day | 22 | 23 | 24 | 25 | | | |
| Composition | C | C | C | C | | | |
| Day | 26 | 27 | 28 | 29 | 30 | | |
| Composition | E | E | E | E | E | | |

EXAMPLE 2:

| Day | 1 | 2 | 3 | 4 | 5 | 6 | 7 |
|---|---|---|---|---|---|---|---|
| Composition | C | C | C | C | C | C | C |
| Day | 8 | 9 | 10 | 11 | 12 | 13 | 14 |
| Composition | C | C | C | C | C | C | C |
| Day | 15 | 16 | 17 | 18 | 19 | 20 | 21 |
| Composition | C | C | C | C | C | C | C |
| Day | 22 | 23 | 24 | 25 | 26 | | |
| Composition | C | C | C | C | C | | |
| Day | 27 | 28 | 29 | 30 | 31 | | |
| Composition | E | E | E | E | E | | |

EXAMPLE 3:

| Day | 1 | 2 | 3 | 4 | 5 | 6 | 7 |
|---|---|---|---|---|---|---|---|
| Composition | C | C | C | C | C | C | C |
| Day | 8 | 9 | 10 | 11 | 12 | 13 | 14 |
| Composition | C | C | C | C | C | C | C |
| Day | 15 | 16 | 17 | 18 | 19 | 20 | 21 |
| Composition | C | C | C | C | C | C | C |
| Day | 22 | 23 | 24 | 25 | | | |
| Composition | C | C | C | C | | | |
| Day | 26 | 27 | 28 | 29 | 30 | 31 | |
| Composition | E | E | E | E | E | E | |

EXAMPLE 4:

| Day | 1 | 2 | 3 | 4 | 5 | 6 | 7 |
|---|---|---|---|---|---|---|---|
| Composition | C | C | C | C | C | C | C |
| Day | 8 | 9 | 10 | 11 | 12 | 13 | 14 |
| Composition | C | C | C | C | C | C | C |
| Day | 15 | 16 | 17 | 18 | 19 | 20 | 21 |
| Composition | C | C | C | C | C | C | C |
| Day | 22 | 23 | 24 | 25 | 26 | 27 | 28 |
| Composition | C | C | C | C | C | C | C |
| Day | 29 | 30 | 31 | 32 | 33 | 34 | 35 |
| Composition | C | C | C | C | C | C | C |
| Day | 36 | 37 | 38 | 49 | 40 | 41 | 42 |
| Composition | C | C | C | C | C | C | C |
| Day | 43 | 44 | 45 | 46 | 47 | 48 | 49 |
| Composition | C | C | C | C | C | C | C |
| Day | 50 | 51 | 52 | 53 | 54 | 55 | 56 |
| Composition | C | C | C | C | C | C | C |
| Day | 1 | 2 | 3 | 4 | 5 | 6 | 7 |
| Composition | C | C | C | C | C | C | C |
| Day | 8 | 9 | 10 | 11 | 12 | 13 | 14 |
| Composition | C | C | 0 | C | C | C | C |
| Day | 15 | 16 | 17 | 18 | 19 | 20 | 21 |
| Composition | C | C | C | C | C | C | C |
| Day | 22 | 23 | 24 | 25 | 26 | 27 | 28 |
| Composition | C | C | C | C | C | C | C |
| Day | 29 | 30 | 31 | 32 | 33 | 34 | 35 |
| Composition | C | C | C | C | C | C | C |
| Day | 36 | 37 | 38 | 49 | 40 | 41 | 42 |
| Composition | C | C | C | C | C | C | C |
| Day | 43 | 44 | 45 | 46 | 47 | 48 | 49 |
| Composition | C | C | C | C | C | C | C |
| Day | 50 | 51 | 52 | 53 | 54 | 55 | 56 |
| Composition | C | C | C | C | C | C | C |
| Day | 57 | 58 | 59 | 60 | 61 | 62 | 63 |
| Composition | E | E | E | E | E | E | E |

EXAMPLE 5:

| Day | 1 | 2 | 3 | 4 | 5 | 6 | 7 |
|---|---|---|---|---|---|---|---|
| Composition | C | C | C | C | C | C | C |
| Day | 8 | 9 | 10 | 11 | 12 | 13 | 14 |
| Composition | C | C | C | C | C | C | C |
| Day | 15 | 16 | 17 | 18 | 19 | 20 | 21 |
| Composition | C | C | C | C | C | C | C |
| Day | 22 | 23 | 24 | 25 | 26 | 27 | 28 |
| Composition | C | C | C | C | C | C | C |
| Day | 29 | 30 | 31 | 32 | 33 | 34 | 35 |
| Composition | C | C | C | C | C | C | C |
| Day | 36 | 37 | 38 | 49 | 40 | 41 | 42 |
| Composition | C | C | C | C | C | C | C |
| Day | 43 | 44 | 45 | 46 | 47 | 48 | 49 |
| Composition | C | C | C | C | C | C | C |
| Day | 50 | 51 | 52 | 53 | 54 | 55 | 56 |
| Composition | C | C | C | C | C | C | C |
| Day | 57 | 58 | 59 | 60 | 61 | 62 | 63 |
| Composition | C | C | C | C | C | C | C |
| Day | 64 | 65 | 66 | 67 | 68 | 69 | 70 |
| Composition | C | C | C | C | C | C | C |
| Day | 71 | 72 | 73 | 74 | 75 | 76 | 77 |
| Composition | C | C | C | C | C | C | C |
| Day | 78 | 79 | 80 | 81 | 82 | 83 | 84 |
| Composition | E | E | E | E | E | E | E |

EXAMPLE 6:

| Day | 1 | 2 | 3 | 4 | 5 | 6 | 7 | |
|---|---|---|---|---|---|---|---|---|
| Composition | C | C | C | C | C | C | C | |
| Day | 8 | 9 | 10 | 11 | 12 | 13 | 14 | |
| Composition | C | C | C | C | C | C | C | |
| Day | 15 | 16 | 17 | 18 | 19 | 20 | 21 | |
| Composition | C | C | C | C | C | C | C | |
| Day | 22 | 23 | 24 | 25 | 26 | 27 | 28 | |
| Composition | C | C | C | C | C | C | C | |
| | | | | | | | | P |
| Day | 29 | 30 | 31 | 32 | 33 | 34 | 35 | |
| Composition | C | C | C | C | C | C | C | |
| | | | | | | | | P |
| Day | 36 | 37 | 38 | 49 | 40 | 41 | 42 | |
| Composition | C | C | C | C | C | C | C | |
| | | | | | | | | P |
| Day | 43 | 44 | 45 | 46 | 47 | 48 | 49 | |
| Composition | C | C | C | C | C | C | C | |
| | | | | | | | | P |

-continued

| Day | 50 | 51 | 52 | 53 | 54 | 55 | 56 |
|---|---|---|---|---|---|---|---|
| Composition | E | E | E | E | E | E | E |

Day = day of the menstrual cycle, day 1 is the first day of bleeding
C = combination of oestrogen and gestagen (= first hormone component)
E = oestrogen (= second hormone component)
P = perforation The formulation of the unit doses is effected in conventional manner with the use of auxiliaries known for the preparation of oestrogen-/gestagen-containing and exclusively oestrogen-containing tablets, pills, dragées etc.

The combined preparation according to the invention serves to prevent conception in women by the administration of daily unit doses of the first hormone component over a minimum of 25 and a maximum of 77 days, commencing on day 1 of the menstrual cycle (first day of menstrual bleeding), followed by 5, 6 or 7 daily unit doses of the second hormone component, which contains exclusively an oestrogen (E), for a total of a minimum of 30 and a maximum of 84 days in the administration cycle. In the second (next) menstrual cycle, administration of the first unit dose of the first hormone component of a new pack unit (kit) of the pharmaceutical combined preparation according to the invention is commenced on day one of that cycle, without any pause in administration.

With that combined preparation, pronounced ovarian suppression without frequent follicle ripening, and also excellent cycle control, can be achieved with a low daily oestrogen dose, a low total amount of oestrogen and a low total amount of hormone per administration cycle.

The advantages of that combined preparation according to the invention (ovulation-inhibiting agent) administered over a minimum of 30 and a maximum of 84 days per cycle compared with the preparations described hitherto, especially those having a daily ethynyloestradiol dose of less that 30 μg and those with a pill-free period, may be characterised as follows:

1. A significantly lower frequency of follicle development in the user. This means a lower risk of breakthrough ovulation and consequently a greater contraceptive reliability especially where mistakes are made in administration.
2. The recruitment of the dominant follicle is effectively suppressed by the extension of the administration of the combination.
3. The administration of 5, 6 or 7 daily oestrogen unit doses following the administration of the combination dose of the first stage results in a clearly improved cycle control and in a lower incidence of side effects, such as headaches within the framework of premenstrual syndrome.
4. Other clinical symptoms that are attributable to strongly fluctuating endogenous levels of oestrogen, such as, for example, tenderness of the breasts, are likewise distinctly reduced on account of the significantly stronger ovarian suppression.
5. As a result of the freedom from bleeding (amenorrhoea) for a longer period, there is an increased acceptance by the user; this is true especially as the number of unit doses in the first stage increases.
6. The negative effects that occur with or as a result of bleeding, such as, for example, anaemia, cramp, queasiness etc. occur less frequently.
7. Constant low oestrogen and gestagen levels; consequent avoidance of metabolic variations and as a result improvement of tolerability.
8. A possible pregnancy as a result of mistakes in administration is recognisable by the absence of withdrawal bleeding after stopping the oestrogen-) and gestagen-containing unit doses.

The formulation of an oestrogen and gestagen for the preparation of a combined preparation according to the invention is effected in a manner completely analogous to that already known for conventional oral contraceptives having a 21-day administration period of active ingredients, such as, for example, Femovan® (ethynyloestradiol/gestodene) or Microgynon® (ethynyloestradiol/levonorgestrel). The formulation of the exclusively oestrogen-containing unit doses can also be carried out in a completely analogous manner to that known for oestrogen-containing agents designed for oral administration that are already available, for example ProgynonC®. The unit doses of the first stage of the preparation according to the invention may also be in the form of a plaster (transdermal application), an implant or another depot formulation and thus administered continuously.

As a form of packing for the combined preparation according to the invention, a blister pack constructed in the manner according to the invention is generally used; other forms of packing known for that purpose are, however, also possible.

In order to determine equivalently effective amounts of ethynyloestradiol and 17β-oestradiol on the one hand and of different gestagens, such as gestodene, levonorgestrel, desogestrel and 3-ketodesogestrel, on the other hand, reference is made to the data given in EP-A-0 253 607. Further details for determining dosage equivalents of different gestagenic active ingredients may be found, for example, in "Probleme der Dosisfindung: Sexualhormone" (Problems of dosage determination: sexual hormones); F. Neumann et al. in "Arzneimittelforschung" (Drug Research) 27, 2a, 296–318 (1977) and in "Aktuelle Entwicklungen in der hormonal Kontrazeption" (Current developments in hormonal contraception), H. Kuhl in "Gynäcologe" 25: 231–240 (1992).

We claim:

1. Two-stage pharmaceutical combined preparation for hormonal contraception containing at least 30 daily unit doses, which preparation, in its first stage, comprises as hormonal active ingredient a combination of an oestrogen preparation and, in a dose that is sufficient to inhibit ovulation, a gestagen preparation, in single stage form and, in the second stage comprises as hormonal active ingredient an oestrogen preparation only, wherein the first stage comprises a minimum of 25 and a maximum of 77 daily discrete or continuous unit doses and the second stage comprises 5, 6 or 7 daily discrete or continuous unit doses, and wherein the total number of daily units is equal to the total number of days of the desired cycle of a minimum of 30 and a maximum of 84 days.

2. Combined preparation according to claim 1, wherein the first stage comprises 25 or 26 daily unit doses.

3. Combined preparation according to claim 1, wherein the first stage comprises a minimum of 28 and a maximum of 77 daily unit doses.

4. Combined preparation according to claim 3, wherein the first stage comprises 28 daily unit doses.

5. Combined preparation according to claim 3, wherein the first stage comprises 28 plus 7, or 28 plus a multiple of 7, daily unit doses.

6. Combined preparation according to claim 1, wherein the second stage comprises 7 daily unit doses.

7. Combined preparation according to claim 2, wherein the second stage comprises 5 or 6 daily unit doses, so that the combined preparation has a total of 30 or 31 daily unit doses.

8. Combined preparation according to claim 1, wherein the oestrogen of the first stage is selected from the group of compounds 17β-oestradiol, ethynyloestradiol and 17β-oestradiol valerate and the gestagen is selected from the group of compounds dienogest gestodene, levonorgestrel, desogestrel, 3-ketodesogestrel, drospironenone, cyproterone acetate, norgestimate and norethisterone and also the oestrogen of the second hormone component is selected from the group of compounds 17β-oestradiol, ethynyloestradiol and 17β-oestradiol valerate.

9. Combined preparation according to claim 1, wherein the oestrogen of the first stage is contained in each daily unit dose in a dose of from 1.0 to 6.0 mg of 17β-oestradiol, from 0.015 to 0.025 mg of ethynyloestradiol, from 1.0 to 4.0 mg of 17β-oestradiol valerate and the gestagen is contained in each daily unit dose in a dose of from 1.0 to 3.0 mg of dienogest from 0.05 to 0.075 mg of gestodene, from 0.05 to 0.125 mg of levonorgestrel, from 0.06 to 0.15 mg of desogestrel, from 0.06 to 0.15 mg of 3-ketodesogestrel, from 1.0 to 3.0 mg of drospironenone, from 1.0 to 2.0 mg of cyproterone acetate, from 0.2 mg to 0.3 mg of norgestimate from 0.35 to 0.75 mg of norethisterone.

10. Combined preparation according to claim 1, wherein there is contained in each daily unit dose in the second stage an amount of from 1.0 to 6.0 mg of 17β-oestradiol, from 0.002 to 0.04 mg of ethynyloestradiol, from 1.0 to 4.0 mg of 17β-oestradiol valerate.

11. Contraceptive kit containing at least 30 daily unit doses each containing at least one hormonal active ingredient, having a first and a second stage, which kit, in its first stage, comprises as hormonal active ingredient a combination of an oestrogen preparation and, in a dose that is sufficient to inhibit ovulation, a gestagen preparation, in single stage form and, in the second stage comprises as hormonal active ingredient an oestrogen preparation only, wherein the first stage comprises a minimum of 25 and a maximum of 77 daily discrete or continuous unit doses and the second stage comprises 5, 6 or 7 daily discrete or continuous unit doses, and wherein the total number of daily units is equal to the total number of days of the desired cycle of a minimum of 30 and a maximum of 84 days.

12. Contraceptive kit according to claim 11, wherein the first stage comprises 25 or 26 daily unit doses.

13. Contraceptive kit according to claim 11, wherein the first stage comprises a minimum of 28 and a maximum of 77 daily unit doses.

14. Contraceptive kit according to claim 13, wherein the first stage comprises 28 daily unit doses.

15. Contraceptive kit according to claim 13, wherein the first stage comprises 28 plus 7, or 28 plus a multiple of 7, daily unit doses.

16. Contraceptive kit according to claim 11, wherein the second stage comprises 7 daily unit doses.

17. Contraceptive kit according to claim 12, wherein the second stage comprises 5 or 6 daily unit doses, so that the kit has a total of 30 or 31 daily unit doses.

18. Contraceptive kit according to claim 11, wherein the oestrogen of the first stage is selected from the group of compounds 17β-oestradiol, ethynyloestradiol and 17β-oestradiol valerate and the gestagen is selected from the group of compounds dienogest gestodene, levonorgestrel, desogestrel, 3-ketodesogestrel, drospironenone, cyproterone acetate, norgestimate and norethisterone and also the oestrogen of the second hormone component is selected from the group of compounds 17β-oestradiol, ethynyloestradiol and 17β-oestradiol valerate.

19. Contraceptive kit according to claim 11, wherein the oestrogen of the first stage is contained in each daily unit dose in a dose of from 1.0 to 6.0 mg of 17β-oestradiol, from 0.015 to 0.025 mg of ethynyloestradiol, from 1.0 to 4.0 mg of 17β-oestradiol valerate and the gestagen is contained in each daily unit dose in a dose of from 1.0 to 3.0 mg of dienogest from 0.05 to 0.075 mg of gestodene, from 0.05 to 0.125 mg of levonorgestrel, from 0.06 to 0.15 mg of desogestrel, from 0.06 to 0.15 mg of 3-ketodesogestrel, from 1.0 to 3.0 mg of drospironenone, from 1.0 to 2.0 mg of cyproterone acetate, from 0.2 mg to 0.3 mg of norgestimate from 0.35 to 0.75 mg of norethisterone.

20. Contraceptive kit according to claim 11, wherein there is contained in each daily unit dose in the second stage an amount of from 1.0 to 6.0 mg of 17β-oestradiol, from 0.002 to 0.04 mg of ethynyloestradiol, from 1.0 to 4.0 mg of 17β-oestradiol valerate.

21. Contraceptive kit containing at least 30 daily unit doses each containing at least one hormonal active ingredient, having a first and a second stage, which kit, in its first stage, comprises as hormonal active ingredient a combination of an oestrogen preparation and, in a dose that is sufficient to inhibit ovulation, a gestagen preparation, in single stage form and, in its second stage comprises as hormonal active ingredient an oestrogen preparation only, wherein the first stage comprises a minimum of 25 and a maximum of 77 daily discrete or continuous unit doses and the second stage comprises 5, 6 or 7 daily discrete or continuous unit doses, and wherein the total number of daily units is equal to the total number of days of the desired cycle of a minimum of 30 and maximum of 84 days, some of the unit doses of the first stage being arranged in periodically repeating sub-units that are separated from one another spatially and/or by other markings.

22. Contraceptive kit according to claim 21, wherein the unit doses are arranged in sub-units at the earliest from the 26th daily unit dose.

23. Contraceptive kit according to claim 21, wherein the individual sub-units can be separated from one another by perforations or other means suitable for separation.

24. Contraceptive kit according to claim 21, wherein the separate sub-units each contain 7 unit doses.

25. Contraceptive kit according to claim 21, wherein the first stage comprises 28 plus 7, or 28 plus a multiple of 7, daily unit doses.

26. Contraceptive kit according to claim 21, wherein the second stage comprises 7 daily unit doses.

27. Contraceptive kit according to claim 21, wherein the oestrogen of the first stage is selected from the group of compounds
17β-oestradiol,
ethynyloestradiol and
17β-oestradiol valerate
and the gestagen is selected from the group of compounds
dienogest
gestodene,
levonorgestrel,
desogestrel,
3-ketodesogestrel,
drospironenone,
cyproterone acetate,
norgestimate and
norethisterone and also
the oestrogen of the second hormone component is selected from the group of compounds
17β-oestradiol,
ethynyloestradiol and
17β-oestradiol valerate.

28. Contraceptive kit according to claim 21, wherein the oestrogen of the first stage is contained in each daily unit dose in a dose of
from 1.0 to 6.0 mg of 17β-oestradiol,
from 0.015 to 0.025 mg of ethynyloestradiol,
from 1.0 to 4.0 mg of 17β-oestradiol valerate
and the gestagen is contained in each daily unit dose in a dose of
from 1.0 to 3.0 mg of dienogest
from 0.05 to 0.075 mg of gestodene,
from 0.05 to 0.125 mg of levonorgestrel, from 0.06 to 0.15 mg of desogestrel,
from 0.06 to 0.15 mg of 3-ketodesogestrel,
from 1.0 to 3.0 mg of drospironenone,
from 1.0 to 2.0 mg of cyproterone acetate,
from 0.2 mg to 0.3 mg of norgestimate
from 0.35 to 0.75 mg of norethisterone.

29. Contraceptive kit according to claim 21, wherein there is contained in each daily unit dose in the second stage an amount of
from 1.0 to 6.0 mg of 17β-oestradiol,
from 0.002 to 0.04 mg of ethynyloestradiol,
from 1.0 to 4.0 mg of 17β-oestradiol valerate.

30. Method of contraception in female mammals comprising a sequential administration for a minimum of 30 and a maximum of 84 days of daily unit doses of a minimum of 25 and a maximum of 77 daily discrete or continuous unit doses during a first stage and 5, 6 or 7 daily discrete or continuous unit doses during a second stage, comprising as hormonal active ingredient in the first stage a combination of an oestrogen preparation and, in a dose that is sufficient to inhibit ovulation, a gestagen preparation, in single stage form, and comprising as hormonal active ingredient in the second stage an oestrogen preparation only.

31. Method according to claim 30, wherein in the first stage 25 or 26 daily unit doses are administered.

32. Method according to claim 30, wherein in the first stage a minimum of 28 and a maximum of 77 daily unit doses are administered.

33. Method according to claim 32, wherein in the first stage 28 daily unit doses are administered.

34. Method according to claim 32, wherein in the first stage 28 plus 7, or 28 plus a multiple of 7, daily unit doses are administered.

35. Method according to claim 30, wherein in the second stage 7 daily unit doses are administered.

36. Method according to claim 31, wherein in the second stage 5 or 6 daily unit doses are administered.

37. Method according to claim 30, wherein the oestrogen in the unit doses of the first stage is selected from the group of compounds
17β-oestradiol,
ethynyloestradiol and
17β-oestradiol valerate
and the gestagen is selected from the group of compounds
dienogest
gestodene,
levonorgestrel,
desogestrel,
3-ketodesogestrel,
drospironenone,
cyproterone acetate,
norgestimate and
norethisterone and also
the oestrogen in the unit doses of the second hormone component is selected from the group of compounds
17β-oestradiol,
ethynyloestradiol and
17β-oestradiol valerate.

38. Method according to claim 30, wherein the oestrogen of the first stage is administered in each daily unit dose in a dose of
from 1.0 to 6.0 mg of 17β-oestradiol,
from 0.015 to 0.025 mg of ethynyloestradiol,
from 1.0 to 4.0 mg of 17β-oestradiol valerate
and the gestagen is administered in each daily unit dose in a dose of from 1.0 to 3.0 mg of dienogest
from 0.05 to 0.075 mg of gestodene,
from 0.05 to 0.125 mg of levonorgestrel,
from 0.06 to 0.15 mg of desogestrel,
from 0.06 to 0.15 mg of 3-ketodesogestrel,
from 1.0 to 3.0 mg of drospironenone,
from 1.0 to 2.0 mg of cyproterone acetate,
from 0.2 mg to 0.3 mg of norgestimate
from 0.35 to 0.75 mg of norethisterone.

39. Method according to claim 30, wherein there is administered in each daily unit dose in the second stage an amount of from 1.0 to 6.0 mg of 17β-oestradiol,
from 0.002 to 0.04 mg of ethynyloestradiol,
from 1.0 to 4.0 mg of 17β-oestradiol valerate.

40. Method according to claim 30 in which the female mammal is a homo sapiens.

* * * * *